United States Patent [19]

Kukolja

[11] 4,165,315
[45] Aug. 21, 1979

[54] SULFINYL HALIDES AND THEIR PREPARATION FROM PENICILLIN SULFOXIDES

[75] Inventor: Stjepan Kukolja, Indianapolis, Ind.

[73] Assignee: Eli Lilly and Company, Indianapolis, Ind.

[21] Appl. No.: 852,251

[22] Filed: Nov. 17, 1977

Related U.S. Application Data

[60] Division of Ser. No. 673,017, Apr. 2, 1976, Pat. No. 4,081,440, which is a continuation-in-part of Ser. No. 632,732, Nov. 19, 1975, abandoned, which is a continuation-in-part of Ser. No. 536,273, Dec. 24, 1974, abandoned.

[51] Int. Cl.$^2$ .................. C07D 205/08; C07D 501/10
[52] U.S. Cl. ......................... 260/239 A; 260/307 H; 260/330.3; 260/326 S; 260/326.37; 548/301; 544/18

[58] Field of Search .... 260/239 AL, 307 H, 332.2 H; 548/301

[56] References Cited

PUBLICATIONS

Ishimaru et al., Bul. Chem. Soc., Japan 48, 2989–2990.
Chou et al., J. Amer. Chem. Soc. 96, 1609–1610 (1974).

Primary Examiner—Mark L. Berch
Attorney, Agent, or Firm—William C. Martens, Jr.; Everet F. Smith

[57] ABSTRACT

A penicillin sulfoxide ester is reacted with an N-chloro halogenating agent at a temperature of from about 75° C. to about 135° C. to produce a novel 2-chlorosulfinylazetidin-4-one intermediate. The intermediate can be treated with stannic chloride to produce a 3-exomethylenecepham sulfoxide.

19 Claims, No Drawings

SULFINYL HALIDES AND THEIR PREPARATION FROM PENICILLIN SULFOXIDES

CROSS REFERENCE

This is a division, of application Ser. No. 673,017 filed Apr. 2, 1976, now U.S. Pat. 4,081,440 which is a continuation-in-part of application Ser. No. 632,732 filed Nov. 19, 1975, and now abandoned, which is a continuation-in-part of application Ser. No. 536,273 filed Dec. 24, 1974, and now abandoned.

BACKGROUND OF THE INVENTION

In the recently issued U.S. Pat. No. 3,843,682 there is disclosed a process for preparing 3-methyl-2-(2-chlorosulfinyl-4-oxo-3-imido-1-azetidinyl)-3-butenoate esters, variously termed "2-chlorosulfinyl-3-imido-azetidin-4-ones". These compounds are prepared from the corresponding penicillin sulfoxide esters by reaction of the latter with sulfuryl chloride at a temperature of from about 75° C. to about 120° C. The compounds which are prepared by this known process are exclusively the 3-imido substituted 2-chlorosulfinylazetidin-4-ones since the process is limited to the use of the 6-imido penicillin sulfoxide esters as starting material. There is no disclosure of the use of or the possibility to use what would be preferred and more readily available, that is, the 6-amido penicillin sulfoxide esters, including the conveniently obtainable penicillin sulfoxide derivatives of the naturally occurring Penicillin G and/or Penicillin V. When one attempts to carry out the reaction disclosed in U.S. Pat. No. 3,843,682 using a 6-amido penicillin sulfoxide ester as starting material, the product which is obtained is a complex mixture containing no 2-chlorosulfinylazetidin-4-one product, or, at most, the latter in a quantity so minute as to be undetectable by ordinary analytical techniques. Therefore, this previously disclosed method, since it requires the absence of an amide hydrogen in the 6-position of the penicillin sulfoxide starting material, has inherent and significant drawbacks since it requires, first, displacement of the naturally occurring 6-substituent of a penicillin by an imido substituent, and, secondly, cleavage of the imido substituent in order to permit reacylation to introduce the substituent of the intended final antibiotic product. It now has been discovered that it is possible to prepare sulfinyl chloride intermediates from 6-amido penicillin sulfoxide esters by altering the conditions of reaction as well as the halogenating agent which is employed. This thereby avoids the previously recognized necessity to block the amide hydrogen in the 6-position of the penicillin sulfoxide starting material by conversion to an amide derivative. It is to such a process as well as to hitherto unavailable compounds produced therefrom that this invention is directed.

The 2-chlorosulfinylazetidin-4-ones produced by the process of this invention can be ring closed to produce a 3-exomethylenecephem sulfoxide ester. Cyclization of the 2-chlorosulfinylazetidin-4-ones to their corresponding 3-exomethylenecepham sulfoxides is accomplished by a FriedelCrafts catalyst induced intramolecular reaction involving the sulfinyl chloride and olefinic moieties of the azetidin4-one starting material.

SUMMARY OF THE INVENTION

It is an object of this invention therefore to provide a process for preparing a sulfinyl chloride of the formula

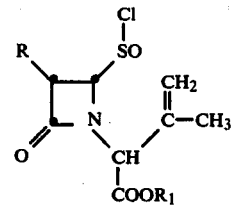

which comprises reacting a penicillin sulfoxide of the formula

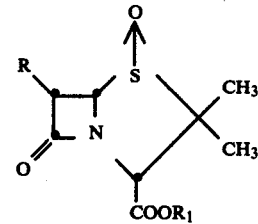

with an N-chloro halogenating agent at a temperature of from about 75° C. to about 135° C. in an inert solvent and under anhydrous conditions; in which, in the above formulae, $R_1$ is a carboxylic acid protecting group; and R is (1) an imido of the formula

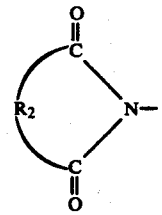

in which $R_2$ is $C_2$-$C_4$ alkenylene or 1,2-phenylene;

(2) an imido group of the formula

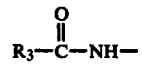

in which $R_3$ is (a) hydrogen, $C_1$-$C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, or $C_1$-$C_4$ alkoxy;

(c) a group of the formula $R''$-$(Q)_m$-$CH_2$- in which R" is R' as defined above, 1,4-cyclohexadienyl, 2-thienyl, or 3-thienyl; m is 0 or 1; and Q is O or S; subject to the limitation that when m is 1, R" is R'; or (d) a group of the formula $$R''-\underset{W}{\underset{|}{CH}}-$$

in which R" is as defined above, and W is protected hydroxy or protected amino;

(3) an imidazolidinyl group of the formula

[structure: imidazolidinyl ring with R", O, N—, CH3, CH3, U substituents]

in which R" is as defined above and U is nitroso or acetyl; or R is (4) an imido group of the formula

[structure: imido group with R7—C(=O), N—, R'—(O)m—CH2—C(=O)]

in which R' is as defined above, m is 0 or 1, and R7 is $C_1-C_3$ alkyl, $C_1-C_3$ haloalkyl, $C_1-C_3$ alkoxy, or 2,2,2-trichloroethoxy.

Another object of this invention relates to novel sulfinyl chlorides having the formula

[structure: β-lactam with R3—C(=O)—NH, Cl, SO, CH2, C—CH3, N, CH, COOR1]

in which R1 is a carboxylic acid protecting group, and R3 is as hereinbefore defined.

DETAILED DESCRIPTION OF THE INVENTION

As delineated hereinabove, the novel sulfinyl chlorides of this invention have the formula

[structure: β-lactam with R3—C(=O)—NH, Cl, SO, CH2, C, N, CH, CH3, COOR1]

R1 in the above formula denotes a carboxylic acid protecting group, and, preferably, one which is removable by acid treatment or by hydrogenation. Preferred carboxylic acid protecting groups include, for example, $C_1-C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2-C_6$ alkanoyloxymethyl, dimethylallyl, phenacyl, or p-halophenacyl, in any of the above of which halo denotes chlorine, bromine or iodine.

Specific illustrations of the preferred carboxylic acid protecting groups of the sulfinyl chlorides of this invention include, for example, methyl, ethyl, n-propyl, isopropyl, n-butyl, sec-butyl, isobutyl, t-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred carboxylic acid protecting groups are methyl, benzyl, p-nitrobenzyl, p-methoxybenzyl, benzhydryl, and 2,2,2-trichloroethyl.

The amide function of the novel sulfinyl chlorides of this invention has the formula $$R_3-\overset{O}{\underset{\|}{C}}-NH-.$$

A preferred subclass of this amide function comprises those moieties in which R3 is (a) hydrogen, $C_1-C_3$ alkyl, halomethyl, cyanomethyl, benzyloxy, 4-nitrobenzyloxy, t-butyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1-C_4$ alkyl, or $C_1-C_4$ alkoxy; or (c) a group of the formula R"—(Q)m—CH2— in which R" and R' as defined above, 1,4-cyclohexadienyl, 2-thienyl, or 3-thienyl; m is 0 or 1; and Q is O or S; subject to the limitation that when m is 1, R" is R'.

Specific illustrations of the group R3 include, for example, hydrogen, methyl, ethyl, n-propyl, isopropyl, chloromethyl, bromomethyl, cyanomethyl, benzyloxy, 4-nitrobenzyloxy, t-butyloxy, 2,2,2-trichloroethoxy, 4-methoxybenzyloxy, phenyl, 2-chlorophenyl, 3,4-dichlorophenyl, 3-chloro-4-fluorophenyl, 3-formyloxyphenyl, 4-nitrophenyl, 2-cyanophenyl, 4-trifluoromethylphenyl, 3-methylphenyl, 2-ethylphenyl, 4-n-propylphenyl, 4-t-butylphenyl, 2-methoxyphenyl, 4-ethoxyphenyl, 3-isopropyloxyphenyl, 4-isobutyloxyphenyl, 1,4-cyclohexadienylmethyl, benzyl, 3-bromobenzyl, 2,5-dichlorobenzyl, 4-chloroacetoxybenzyl, 2-nitrobenzyl, 3-cyanobenzyl, 4-trifluoromethylbenzyl, 3-methylbenzyl, 4-n-butylbenzyl, 2-methoxybenzyl, 3-isopropoxybenzyl, phenoxymethyl, 3-iodophenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 4-trimethylsilyloxyphenoxymethyl, 3-nitrophenoxymethyl, 4-cyanophenoxymethyl, 2-trifluoromethylphenoxymethyl, 3-methylphenoxymethyl, 4-n-propylphenoxymethyl, 4-n-butylphenoxymethyl, 3-methoxyphenoxymethyl, 4-ethoxyphenoxymethyl, phenylthiomethyl, 3-iodophenylthiomethyl, 4-fluorophenylthiomethyl, 3-benzyloxyphenylthiomethyl, 4-benzhydryloxyphenylthiomethyl, 3-trityloxyphenylthiomethyl, 4-nitrobenzyloxyphenylthiomethyl, 4-trimethylsilyloxyphenylthiomethyl, 3-nitrophenylthiomethyl, 4-cyanophenylthiomethyl, 2-trifluoromethylphenylthiomethyl, 3-methylphenylthiomethyl, 4-n-propylphenylthiomethyl, 4-n-butylphenylthiomethyl, 3-methoxyphenylthiomethyl, 4-ethoxyphenylthiomethyl, α-(benzhydryloxy)-thien-2-ylmethyl, α-(4-nitrobenzyloxy)-thien-2-ylmethyl, α-(t-butyloxycarbonylamino)-thien-2-ylmethyl, α-(formyloxy)-thien-3-ylmethyl, α-(benzyloxy)-thien-3-ylmethyl, α-(benzyloxycarbonylamino)-thien-3-ylmethyl, α-(chloroacetoxy)-thien-2-ylmethyl, α-(t-butyloxy)-thien-2-ylmethyl, α-(4-nitrobenzyloxycarbonylamino)-thien-2-ylmethyl, α-trityloxybenzyl, α-(4-methoxybenzyloxy)benzyl, α-(2,2,2-trichloroethoxycarbonylamino)benzyl, α-(trimethylsilyloxy)-4-bromobenzyl, α-(benzhydryloxycarbonylamino)-3-chlorobenzyl, α-(trimethylsilylamino)-4-fluorobenzyl, α,4-di(formyloxy)benzyl, α-(4-nitrobenzyloxycarbonylamino)-3-chloroacetoxybenzyl, α-(4-methoxybenzyloxycarbonylamino)-4-benzhydryloxybenzyl, α-benzyloxy-3-nitrobenzyl, α-(4-nitrobenzyloxy)-2-cyanobenzyl, -(t-butoxycarbonylamino)--(t-butyoxycarbonylamino)-4-trifluoromethylbenzyl, α-formyloxy-4-methylbenzyl, α-benzyloxycarbonylamino-3-n-butylbenzyl, α-(benzyloxycarbonylamino)-4-methoxybenzyl, α-formyloxy-3-isopropoxybenzyl, thien-2-ylmethyl, thien-3-ylmethyl, 3-(2-chlorophenyl)-5-methylisoxazol-4-yl, and the like.

Of the groups defined by the term R$_3$, those which are especially preferred are those of the formula R"-(Q)$_m$—CH$_2$—. Of the latter class, highly preferred groups are those in which R" is 2-thienyl, phenyl, or substituted phenyl. When R" is phenyl or substituted phenyl, it is more preferred that, when m is 1, Q is oxygen.

In portions of the definition provided herein for the group R$_3$, the terms "protected amino", "protected hydroxy", and "protected carboxy" are employed.

The term "protected amino", when employed herein, refers to an amino group substituted with one of the commonly employed amino blocking groups such as t-butyloxycarbonyl, benzyloxycarbonyl, 4-methoxybenzyloxycarbonyl, 4-nitrobenzyloxycarbonyl, 2,2,2-trichloroethoxycarbonyl, 1-carbomethoxy-2-propenyl formed with methyl acetoacetate, trimethylsilyl, and the like. Additional typical amino protecting groups are described by J. W. Barton in *Protective Groups in Organic Chemistry*, J. F. W. McOmie, Ed., Plenum Press, New York, N. Y., 1973, Chapter 2. Any of these are recognized as useful within the meaning of the term "protected amino" employed herein.

The term "protected hydroxy", when employed herein, refers to the readily cleavable groups formed with an hydroxyl group such as a formyloxy group, a chloroacetoxy group, a benzyloxy group, a benzhydryloxy group, a trityloxy group, a 4-nitrobenzyloxy group, a trimethylsilyloxy group, and the like. Other hydroxy protecting groups, including those described by C. B. Reese in *Protecting Groups in Organic Chemistry*, supra, Chapter 3, are considered to be within the term "protected hydroxy" as used herein.

The terms "protected carboxy" and "carboxylic acid protecting group", when employed herein, refer to a carboxy group which has been protected by one of the commonly used carboxylic acid protecting groups employed to block or protect the carboxylic acid functionality of a compound while a reaction or sequence of reactions involving other functional sites of the compound are carried out. Such protected carboxy groups are noted for their ease of cleavage to the corresponding carboxylic acid by hydrolytic or by hydrogenolytic methods. Examples of carboxylic acid protecting groups include methyl, t-butyl, benzyl, 4-methoxybenzyl, C$_2$-C$_6$ alkanoyloxymethyl, 2-iodoethyl, 4-nitrobenzyl, diphenylmethyl (benzhydryl), phenacyl, p-halophenacyl, dimethylallyl, 2,2,2-trichloroethyl, succinimidomethyl and like ester forming moieties. The nature of such ester forming groups is not critical so long as the ester formed therewith is stable under the reaction conditions of the process of this invention. Furthermore, other known carboxy protecting groups such as those described by E. Haslam in *Protective Groups in Organic Chemistry*, supra, Chapter 5, are considered to be within the term "protected carboxy" as used herein.

Preferred groups within the term "protected carboxy" are tert-butyl, 4-methoxybenzyl, 4-nitrobenzyl, benzhydryl, and 2,2,2-trichloroethyl.

In the foregoing definitions, hydroxy, amino, and carboxy protecting groups, of course, are not exhaustively described. The function of these groups is to protect reactive functional groups during preparation of a desired product. They then are removed without disruption of the remainder of the molecule. Many such protecting groups are well known in the art, and their use is equally applicable in the process of this invention. Likewise, compounds containing these groups participate in the invention defined herein.

Although in the compound aspect of this invention the group R is restricted to the amide substituent of the formula

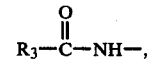

the process aspect of this invention also can be carried out using penicillin sulfoxides having the formula in which R is a cyclic imido group of the formula

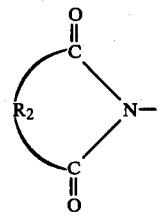

This cyclic imide group, defined by R$_2$ taken together with the nitrogen-carbonyl combination to which it is bonded, can be formed by reacting the 6-amino group of 6-aminopenicillanic acid (6-APA) or an ester of 6-APA with a dicarboxylic acid or anhydride or other reactive variant thereof, followed by reacting the resulting derivative with a C$_1$ to C$_4$ alkyl haloformate, for example, ethyl chloroformate, in the presence of an organic base. R$_2$ is C$_2$-C$_4$ alkenylene or 1,2-phenylene and can be considered as being the residue of a dicarboxylic acid, the cyclic imide thus represented being prepared from such dicarboxylic acid, its anhydride, or an appropriate reactive variant thereof. Cyclic imides an be prepared, for example, from acids such as maleic, methylmaleic, phthalic, and the like, or their respective anhydrides, as well as related compounds and compounds of similar reactivities. Additional examples of cyclic anhydrides of the type defined are found in the prior art such as in the *Journal of Organic Chemistry*, Volume 26, pp. 3365–3367 (September, 1961). 6-Phthalimidopenicillanic acid can also be prepared from 6-APA and N-carboethoxyphthalimide according to the procedure of Y. G. Perron et al., *Journal of Medicinal Chemistry,* Volume 5, (1962), p. 1016.

Moreover, the group R in the process aspect of this invention can be an imido group of the formula

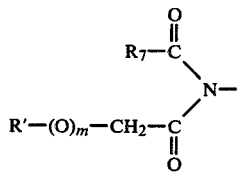

in which R' is phenyl or phenyl substituted with 1 or 2 halogens, protected hydroxy, nitro, cyano, trifluoromethyl, $C_1$–$C_4$ alkyl, or $C_1$–$C_4$ alkoxy; m is 0 or 1; and $R_7$ is $C_1$–$C_3$ alkyl, $C_1$–$C_3$ haloalkyl, $C_1$–$C_3$ alkoxy, or 2,2,2-trichloroethoxy.

The imido group thus defined represents a diacylamino group in which one of the acylamino moieties contains the group R'-(O)$_m$-CH$_2$- and thus is specifically illustrated by groups described hereinbefore.

The other acylamino moiety contains the group $R_7$ which includes, for example, methyl, ethyl, n-propyl, isopropyl, chloromethyl, bromomethyl 2-chloroethyl, 2-iodoethyl, 3-chloropropyl, 2-chloropropyl, 1-chloropropyl, 2-bromoethyl, fluoromethyl, 2-fluoroethyl, methoxy, ethoxy, n-propoxy, isopropoxy, 2,2,2-trichloroethoxy, and the like.

In addition, the group R in the process aspect of this invention can be an imidazolidinyl group of the formula

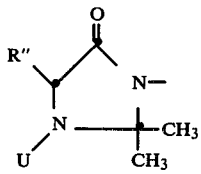

in which U is nitroso or acetyl and R' is 1,4-cyclohexadienyl, 2-thienyl, 3-thienyl, phenyl, or phenyl substituted with 1 or 2 halogens, protected hydroxy, nitro, cyano, trifluoromethyl, $C_1$–$C_4$ alkyl, or $C_1$–$C_4$ alkoxy.

The group thus represented is a 2,2-dimethyl-3-nitroso-5-oxo-4-(substituted)-imidazolidin-1-yl group or a 2,2-dimethyl-3-acetyl-5-oxo-4-(substituted-imidazolidin-1-yl group, and the 4-substituent (R'') in the imidazolidinyl formula typically includes 1,4-cyclohexadienyl, thien-2-yl, thien-3-yl, phenyl, 3-bromophenyl, 2-chlorophenyl, 4-fluorophenyl, 3-iodophenyl, 3-chloro-4-fluorophenyl, 2-chloro-4-bromophenyl, 4-formyloxyphenyl, 3-formyloxyphenyl, 4-nitrophenyl, 2-cyanophenyl, 3-trifluoromethylphenyl, 4-methylphenyl, 3-ethylphenyl, 4-isopropylphenyl, 4-t-butylphenyl, 3-methoxyphenyl, 2-ethoxyphenyl, 4-n-propoxyphenyl, 3-isopropoxyphenyl, 4-isobutoxyphenyl, and the like.

The penicillin sulfoxide starting materials of the process of this invention in which R is the aforedescribed imidazolidinyl group can be prepared in accordance with known techniques by reacting a penicillin of the formula

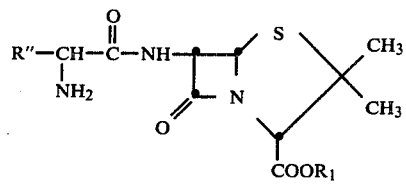

or its corresponding free acid with acetone under moderately basic conditions to produce the labile intermediate of the formula

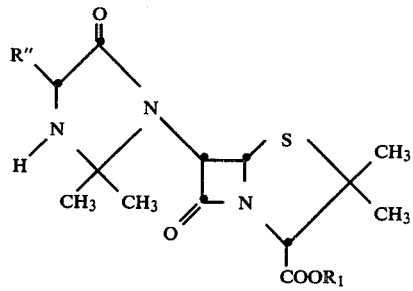

This product then is converted to the stable N-nitroso or N-acetyl derivative in which R is the aforedescribed imidazolidinyl group by treating the product with sodium nitrite or acetic anhydride under acidic conditions and with cooling. The resulting product then can be oxidized to the corresponding sulfoxide by well recognized techniques. These preparations are detailed in Gottstein et al., J. Org. Chem., 37, (1972) 2765; and Heusler, *Helvetica Chimica Acta,* 55 (1972) 388.

As will be apparent to those of ordinary skill in the penicillin and cephalosporin arts, any of the penicillin sulfoxide starting materials used in the process of this invention are readily preparable from available penicillin sources such as naturally occurring Penicillin G and/or Penicillin V. 6-Aminopenicillanic acid (6-APA) can be prepared from either of the above naturally-occurring penicillins by cleavage of the 6-acyl function employing techniques well known in the art.

It is possible to prepare, by widely recognized techniques and from 6-APA, any of the starting materials of the process of this invention. For example, 6-APA can be converted to the desired ester by esterification of the 3-carboxyl function employing any of several typical esterification techniques.

Furthermore, the amino group of 6-APA can be acylated to produce any of the groups defined herein by the term R. This is achieved by reacting 6APA with an activated form of the acid of the intended acyl group. Such activated forms include the corresponding acid halides, anhydrides, or activated esters, such as the pentachlorophenyl ester.

Likewise the penicillin can be oxidized to the sulfoxide under any of a wide variety of recognized conditions, including treatment of the penicillin with m-chloroperbenzoic acid or sodium periodate.

These conversions, cleavage to 6-APA, esterification, acylation, and oxidation, can be carried out in any sequence consistent with the intended structural modifications. In any event, all such conversions can be accomplished employing techniques, conditions, and reagents readily available to and well recognized by one of ordinary skill in the art.

Preferred penicillin sulfoxide esters for use in the process of this invention are those having the formula

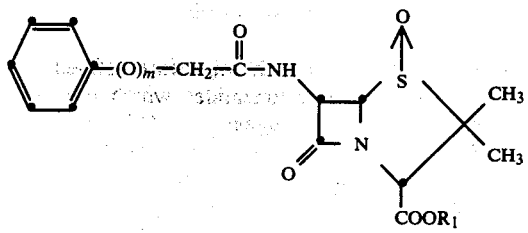

in which m is 0 or 1 and $R_1$ is a carboxylic acid protecting group.

Correspondingly, the preferred sulfinyl chlorides of this invention are those of the formula

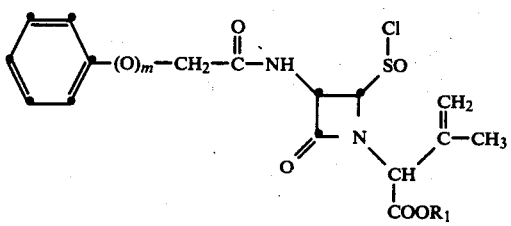

in which m is 0 or 1, and $R_1$ is a carboxylic acid protecting group.

Other preferred penicillin sulfoxide esters for use in the process of this invention are those of the formula

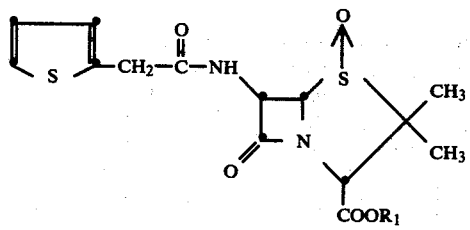

in which $R_1$ is a carboxylic acid protecting group.

Correspondingly, other preferred sulfinyl chlorides of this invention are those of the formula

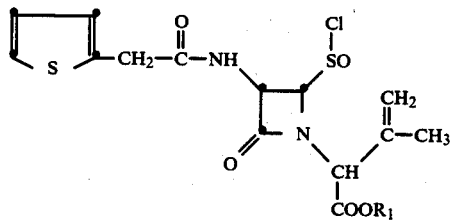

in which $R_1$ is a carboxylic acid protecting group.

The sulfinyl chlorides produced by the process of this invention, some of which are novel, result from the interaction of a penicillin sulfoxide ester with an N-chloro halogenating agent at an elevated temperature.

By the term "N-chloro halogenating agent" is meant a reagent having at least one chlorine bonded directly to a nitrogen atom with the remaining moiety or moieties of the structure of the reagent having electron-withdrawing strength sufficient to produce, as by-product from the sulfinyl chloride preparation, a nitrogen-containing compound which exhibits the following characteristics. The thus-produced nitrogen-containing compound, first, will be one which corresponds to the N-chloro halogenating agent but which has the chlorine atom replaced by a hydrogen atom. Secondly, the nitrogen-containing compound, due primarily to the properties of the electron-withdrawing moiety, will be inert to the sulfinyl chloride product.

The N-chloro halogenating agents which are employed in the process of this invention preferably are compounds of the formula

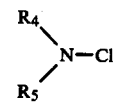

in which $R_4$ is hydrogen, chloro, $C_1$–$C_3$ alkyl, cyclohexyl, phenyl, or phenyl substituted with chloro, bromo, methyl, or nitro, and $R_5$ is $R_6$-X- in which $R_6$ is $C_1$–$C_3$ alkyl, cyclohexyl, phenyl, or phenyl substituted with chloro, bromo, methyl, or nitro, and X is

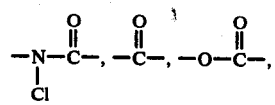

or $-SO_2-$; or $R_4$ and $R_5$ taken together with the nitrogen to which they are bonded define a heterocyclic structure of the formula

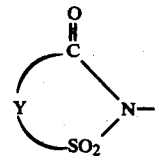

in which Y is o-phenylene, or $-(CH_2)_n-$ in which n is 2 or 3; or a structure of the formula

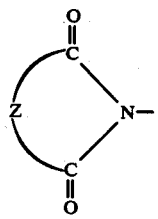

in which Z is Y as hereinbefore defined or a group of the formula

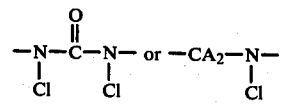

in which A is hydrogen or methyl.

Several types of preferred N-chloro compounds which can be employed in producing the sulfinyl chlorides are described by the above definition. These N-chloro compounds include (a) ureas, (b) amides, (c) urethans, (d) sulfonamides, (e) sulfimides, (f) imides, (g) hydantoins, and (h) isocyanuric acids.

The preferred N-chloro ureas which can be employed in this invention generally have the formula

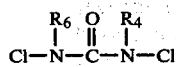

in which R$_4$ is hydrogen, chloro, C$_1$–C$_3$ alkyl, cyclohexyl, phenyl, or phenyl substituted with chloro, bromo, methyl, or nitro, and R$_6$ is C$_1$–C$_3$ alkyl, cyclohexyl, phenyl, or phenyl substituted with chloro, bromo, methyl, or nitro.

Illustrative of these ureas are
N,N'-dichloro-N-methylurea;
N,N'-dichloro-N-ethyl-N'-cyclohexylurea;
N,N'-dichloro-N-phenylurea;
N,N'-dichloro-N,N'-diphenylurea;
N,N'-dichloro-N-(p-tolyl)urea;
N,N'-dichloro-N-(m-chlorophenyl)-N'-methylurea;
N,N'-dichloro-N,N'-dicyclohexylurea;
N,N'-dichloro-N-isopropyl-N'-(p-tolyl)urea;
N,N'-dichloro-N-phenyl-N'-propylurea;
N,N'-dichloro-N-cyclohexyl-N'-(p-nitrophenyl)urea;
N,N,N'-trichloro-N-methylurea;
N,N,N'-trichloro-N-phenylurea; and the like.

The preferred N-chloro amides which can be employed in this invention generally have the formula

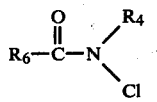

in which R$_4$ and R$_6$ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)-butyramide, N-chlorohexahydrobenzamide, N,2,4-trichloroacetanilide, and the like.

The preferred N-chloro urethans which can be used in preparation of the sulfinyl chlorides in accordance with this invention generally have the formula

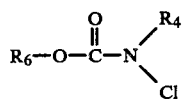

in which R$_4$ and R$_6$ are as hereinbefore defined.

Illustrative of these urethans are methyl N,N-dichlorocarbamate, ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorphenyl N-methyl-N-chlorocarbamate, cyclohexyl N-cyclohexyl-chlorocarbamate, isopropyl N-p-tolyl-N-chlorocarbamate, phenyl N-propyl-N-chlorocarbamate, cyclohexyl N-p-nitrophenyl-N-chlorocarbamate, and the like.

The preferred N-chloro sulfonamides which can be used to prepare the sulfinyl chlorides in accordance with this invention have the formula

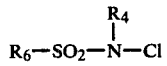

in which R$_4$ and R$_6$ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorbenzenesulfonamide, N-methyl-N-chloro-p-toluenesulfonamide, N-cyclohexyl-N-chlorocyclohexanesulfonamide, N-p-tolyl-N-chloroisopropanesulfonamide, N-propyl-N-chlorobenzenesulfonamide, N-p-nitrophenyl-N-chlorocyclohexanesulfonamide, and the like.

A further preferred type of N-chloro halogenating agent which can be employed in preparation of the sulfinyl chlorides is a sulfimide of the formula

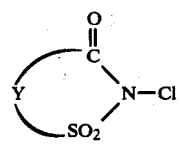

in which Y is o-phenylene, —CH$_2$—CH$_2$—, or —CH$_2$—CH$_2$—CH$_2$—. These compounds include o-sulfobenzoic N-chloroimide, β-sulfopropionic N-chloroimide, and γ-sulfobutyric N-chloroimide.

Also preferred for use as N-chlorohalogenating agents in the preparation of the sulfinyl chlorides in accordance with this invention are N-chloroimides of the formula

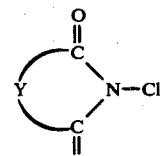

in which Y is o-phenylene, —CH$_2$—CH$_2$—, or —CH$_2$—CH$_2$—CH$_2$—. These compounds include N-chlorophthalimide, N-chlorosuccinimide, and N-chloroglutarimide.

N,N-Dichlorohydantoins can also be employed as halogenating agents in preparing the sulfinyl chlorides in accordance with this invention. These hydantoins have the formula

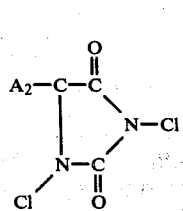

in which A is hydrogen or methyl, and include 1,3-dichlorohydantoin, 1,3-dichloro-5-methylhydantoin, and 1,3-dichloro-5,5-dimethylhydantoin.

Another type of halogenating agent which can be employed is a class of isocyanuric acids which includes N,N', N''-trichloroisocyanuric acid having the formula

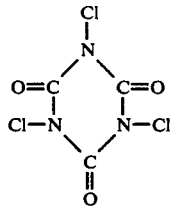

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., J. Org. Chem. 39, (1974) pp. 3136–3138; Theilacker et al., Liebigs Ann. Chem. 703, (1967) pp. 34–36; and Houben-Weyl, Methoden der Organischen Chemie, Volume V/3, pp. 796–810.

N-Chloro halogenating agents which are highly preferred for use in the process of this invention are N-chloro imides, and particularly N-chlorosuccinimide or N-chlorophthalimide.

The reaction of the penicillin sulfoxide with the N-chloro halogenating agent generally is carried out by mixing at least 1 mole and up to about 1.5 moles of the halogenating agent with each mole of the penicillin sulfoxide ester. An even larger excess of the halogenating agent can be employed; however, no advantage is gained thereby. Preferably, therefore, the ratio of reactants is from about 1.0 to about 1.1 moles of halogenating agent per mole of the penicillin sulfoxide ester. The resulting mixture, preferably dissolved in a suitable inert organic solvent, is heated to a temperature of from about 75° C. to about 135° C. Preferably, the temperature of reaction is from about 100° C. to about 120° C., and, most preferably, about 110° C.

By "inert organic solvent" is meant an organic solvent which, under the conditions of sulfinyl chloride formation, does not appreciably react either with the reactants or with the products. Suitable inert organic solvents are those having a boiling point at least as high as the temperature of reaction and include, for example, aromatic hydrocarbons such as benzene, toluene, ethylbenzene, cumene, and the like; halogenated hydrocarbons such as carbon tetrachloride, chlorobenzene, bromoform, bromobenzene, ethylene dichloride, 1,1,2-trichloroethane, ethylene dibromide, and the like; and any other appropriate inert solvents. Preferred solvents are those having a boiling point within the range of the temperature at which the reaction is to be carried out, thereby permitting the reaction mixture to be refluxed while retaining temperature control. Particular conditions of reaction include the use of toluene or 1,1,2-trichloroethane as solvent with the temperature of reaction being that developed under reflux conditions.

A requirement of the process of this invention is that the reaction be carried out under anhydrous conditions. It is not intended by the term "anhydrous conditions" to mean the total absence of any moisture; instead, this term means the avoidance in the reaction mixture of any substantial amount of moisture. This is accomplished by the exercise of any of the recognized procedures for rendering a reaction system anhydrous. The halogenating agent, since it generally will react with water, normally will not be the source of moisture in the reaction mixture; typically, any excessive quantity of moisture in the reaction system arises from the presence of moisture on the solvent which is employed. Generally, therefore, the solvent is pretreated to remove residual amounts of water. The solvent can be rendered anhydrous to the extent herein contemplated by contacting it with a drying agent which will bind moisture and thereby effectively remove it from the solvent. Typical such drying agents include anhydrous sodium sulfate, magnesium sulfate, sodium carbonate, potassium carbonate, calcium carbide, calcium chloride, calcium hydride, potassium sulfate, calcium oxide, molecular sieves, particularly types 3A and 4A, and the like.

In the event that the solvent is one with which water will azeotrope, moisture can be removed by subjecting the solvent to conditions of reflux using known types of chemical equipment including the usual Dean-Stark trap or the Barrett types of water traps which collect the moisture as it azeotropes out of the solvent medium.

The penicillin sulfoxide ester starting material itself may contain moisture. This can be removed by subjecting the penicillin sulfoxide to any of the typical drying techniques, including in vacuo drying in an oven at a low temperature up to about 50° C. Additionally, the penicillin sulfoxide ester can be added to the solvent and the mixture subjected to azeotropic water removal.

The mixture containing the penicillin sulfoxide ester and the N-chloro halogenating agent generally is heated at a temperature in the defined range for a period of from about 0.5 to about 4 hours, and preferably from about 1 to about 2 hours, after which time the sulfinyl chloride can be isolated from the reaction mixture, typically by evaporating the reaction mixture in vacuo to remove the solvent. Although the sulfinyl chloride can be isolated from the reaction mixture, it is not necessary (subject to a limitation discussed hereinbelow) that it be isolated prior to being subjected to further reaction. As indicated hereinabove, the sulfinyl chloride can be employed as an intermediate in the preparation of a 3-exomethylenecepham sulfoxide. When this is intended, the sulfinyl chloride reaction mixture itself can be employed in a manner to be further described hereinafter.

It has also been discovered that in many instances it is desirable to include a non-alkaline acid scavenger in the reaction mixture. For some reason, not yet understood, small amounts of hydrogen chloride can be liberated to the reaction system. A non-alkaline acid scavenger will remain entirely inert in the normal, hydrogen chloride-free reaction medium; however, it will become activated to the extent necessary to react with any generated hydrogen chloride and thereby to remove it from the reaction medium.

Typical non-alkaline acid scavengers include epoxide compounds such as ethylene oxide, propylene oxide, epichlorohydrin, 1,2-epoxy-3-phenoxypropane, and the like. These substances exhibit non-alkaline properties but, nevertheless, will react with and remove acidic substances from a reaction system. A more complete discussion of these reagents is provided in Hunsberger and Tien, Chem. Ind, 88 (1959); and also in Buddrus,

*Angew. Chem. Internat. Edit.,* Vol. 11 (1972), pp. 1041–1050.

The amount of non-alkaline acid scavenger which may be employed in the sulfinyl chloride preparation is not critical. Preferably, however, it should be an amount sufficient at least to account for any hydrogen chloride which may be formed. Although an excess of the non-alkaline acid scavenger can be employed without adverse consequence in the preparation of the sulfinyl chloride, the presence of an excess of the non-alkaline acid scavenger will become significant in those instances in which the reaction mixture containing the sulfinyl cloride product is itself used in conversion to the corresponding 3-exomethylenecepham sulfoxide. Therefore, it is highly preferred that, prior to ring-closure using stannic chloride, the sulfinyl cloride be separated from any excess non-alkaline acid scavenger as well as from any product formed by reaction of the scavenger with hydrogen chloride.

A typical preparation of a sulfinyl chloride in accordance with the process of this invention is accomplished by mixing molar equivalents of the penicillin sulfoxide and the N-chloro halogenating agent in a suitable pre-dried solvent. The resulting mixture is heated to the desired temperature of reaction which preferably is somewhat higher for a 6-amido penicillin sulfoxide starting material than for a 6-imido penicillin sulfoxide starting material. The reaction mixture is heated at the desired temperature of reaction for the intended period of reaction. Preferably, the solvent which is employed is one which permits the temperature of reaction to be achieved and maintained by reflux of the reaction mixture. Upon completion of the reaction time, the reaction is terminated by cooling the mixture to about room temperature, washing the mixture with water, and drying it over a suitable inorganic drying agent. Upon evaporation of the solvent, the sulfinyl chloride product is recovered, generally as an amorphous solid.

As an alternative to the above typical preparation method, the penicillin sulfoxide ester can be dissolved in the selected solvent, the mixture heated to the temperature of reaction, and the N-chloro halogenating agent, either alone or in solution, added dropwise to the heated mixture. Upon completion of the addition, the resulting mixture usually will be allowed to react at the defined conditions. Workup can be similar or identical to that described above.

Examples of sulfinyl chlorides of this invention include:

Methyl 3-methyl-2-(2-chlorosulfinyl-4-oxo-3-maleimido-1-azetidinyl)-3-butenoate;

t-butyl 3-methyl-2-(2-chlorosulfinyl-4-oxo-3-phthalimido-1-azetidinyl)-3-butenoate;

benzyl 3-methyl-2-(2-chlorosulfinyl-4-oxo-3-formamido-1-azetidinyl)-3-butenoate;

2,2,2-trichloroethyl 3-methyl-2-(2-chlorosulfinyl-4-oxo-3-acetamido-1-azetidinyl)-3-butenoate;

p-nitrobenzyl 3-methyl-2-(2-chlorosulfinyl-4-oxo-3-butyramido-1-azetidinyl)-3-butenoate;

p-methoxybenzyl 3-methyl-2-(2-chlorosulfinyl-4-oxo-3-chloroacetamido-1-azetidinyl)-3-butenoate;

benzhydryl 3-methyl-2-[2-chlorosulfinyl-4-oxo-3-cyanoacetamido-1-azetidinyl]-3-butenoate;

p-nitrobenzyl 3-methyl-2-[2-chlorosulfinyl-4-oxo-3-(4-nitrobenzyloxycarbamido)-1-azetidinyl]-3-butenoate;

isobutyl 3-methyl-2-(2-chlorosulfinyl-4-oxo-3-benzyloxycarbamido-1-azetidinyl)-3-butenoate;

ethyl 3-methyl-2-[2-chlorosulfinyl-4-oxo-3-(t-butyloxycarbamido)-1-azetidinyl]-3-butenoate;

2-iodoethyl 3-methyl-2-[2-chlorosulfinyl-4-oxo-3-(2',2',2'-trichloroethoxycarbamido)-1-azetidinyl]-3-butenoate;

acetoxymethyl 3-methyl-2-[2-chlorosulfinyl-4-oxo-3-(4'-methoxybenzyloxycarbamido)-1-azetidinyl]-3-butenoate;

benzyl 3-methyl-2-[2-chlorosulfinyl-4-oxo-3-(2'-thienylacetamido)-1-azetidinyl]-3-butenoate;

ethyl 3-methyl-2-(2-chlorosulfinyl-4-oxo-3-benzamido-1-azetidinyl)-3-butenoate;

phenacyl 3-methyl-2-[2-chlorosulfinyl-4-oxo-3-(4'-chlorobenzamido)-1-azetidinyl]-3-butenoate;

p-chlorophenacyl 3-methyl-2-[2-chlorosulfinyl-4-oxo-3-(3'-formyloxybenzamido)-1-azetidinyl]-3-butenoate;

pivaloyloxymethyl 3-methyl-2-[2-chlorosulfinyl-4-oxo-3-(4'-nitrobenzamido)-1-azetidinyl]-3-butenoate;

isopropyl 3-methyl-2-[2-chlorosulfinyl-4-oxo-3-(2'-cyanobenzamido)-1-azetidinyl]-3-butenoate;

succinimidomethyl 3-methyl-2-[2-chlorosulfinyl-4-oxo-3-(4'-trifluoromethylbenzamido)-1-azetidinyl]-3-butenoate;

phthalimidomethyl 3-methyl-2-[2-chlorosulfinyl-4-oxo-3-(3'-methylbenzamido)-1-azetidinyl]-3-butenoate;

sec-butyl 3-methyl-2-[2-chlorosulfinyl-4-oxo-3-(2'-methoxybenzamido)-1-azetidinyl]-3-butenoate;

n-butyl 3-methyl-2-[2-chlorosulfinyl-4-oxo-3-(1',4'-cyclohexadienylacetamido)-1-azetidinyl]-3-butenoate;

2,2,2-trichloroethyl 3-methyl-2-[2-chlorosulfinyl-4-oxo-3-(2'-thienylacetamido)-1-azetidinyl]-3-butenoate;

p-methoxybenzyl 3-methyl-2-(2-chlorosulfinyl-4-oxo-3-phenylacetamido-1-azetidinyl)-3-butenoate;

2,2,2-trichloroethyl 3-methyl-2-(2-chlorosulfinyl-4-oxo-3-phenoxyacetamido-1-azetidinyl)-3-butenoate;

p-nitrobenzyl 3-methyl-2-[2-chlorosulfinyl-4-oxo-3-(2',5'-dichlorophenylacetamido)-1-azetidinyl]-3-butenoate;

benzyl 3-methyl-2-[2-chlorosulfinyl-4-oxo-3-(3'-bromophenoxyacetamido)-1-azetidinyl]-3-butenoate;

t-butyl 3-methyl-2-[2-chlorosulfinyl-4-oxo-3-(4'-chloroacetoxyphenylacetamido)-1-azetidinyl]-3-butenoate;

isobutyl 3-methyl-2-[2-chlorosulfinyl-4-oxo-3-(3'-formyloxyphenoxyacetamido)-1-azetidinyl]-3-butenoate;

p-nitrobenzyl 3-methyl-2-[2-chlorosulfinyl-4-oxo-3-(2'-nitrophenylacetamido)-1-azetidinyl]-3-butenoate;

p-methoxybenzyl 3-methyl-2-[2-chlorosulfinyl-4-oxo-3-(4'-nitrophenoxyacetamido)-1-azetidinyl]-3-butenoate;

benzhydryl 3-methyl-2-[2-chlorosulfinyl-4-oxo-3-(3'-cyanophenylacetamido)-1-azetidinyl]-3-butenoate;

p-bromophenacyl 3-methyl-2-[2-chlorosulfinyl-4-oxo-3-(2'-cyanophenoxyacetamido)-1-azetidyl]-3-butenoate;

propionoxymethyl-3-methyl-2-[2-chlorosulfinyl-4-oxo-3-(4'-trifluoromethylphenylacetamido)-1-acetidinyl]-3-butenoate;

2,2,2-tribromoethyl 3-methyl-2-[2-chlorosulfinyl-4-oxo-3-(3'-trifluoromethylphenoxyacetamido)-1-azetidinyl]-3-butenoate;

2-iodoethyl 3-methyl-2-[2-chlorosulfinyl-4-oxo-3-(2'-ethylphenylacetamido)-1-azetidinyl]-3-butenoate;

acetoxymethyl 3-methyl-2-[2-chlorosulfinyl-4-oxo-3-(4'-isopropylphenoxyacetamido)-1-azetidinyl]-3-butenoate;

n-butyl 3-methyl-2-[2-chlorosulfinyl-4-oxo-3-(3'-ethoxyphenylacetamido)-1-azetidinyl]-3-butenoate;

p-nitrobenzyl 3-methyl-2-[2-chlorosulfinyl-4-oxo-3-(4'-isopropoxyphenoxyacetamido)-1-azetidinyl]-3-butenoate;

p-nitrobenzyl 3-methyl-2-[2-chlorosulfinyl-4-oxo-3-(α-formyloxyphenylacetamido)-1-azetidinyl]-3-butenoate;

p-methoxybenzyl 3-methyl-2-[2-chlorosulfinyl-4-oxo-3-(α-benzhydryloxyphenylacetamido)-1-azetidinyl]-3-butenoate;

benzyl 3-methyl-2-[2-chlorosulfinyl-4-oxo-3-(2-thienyl-α-benzyloxyacetamido)-1-azetidinyl]-3-butenaote;

benzhydryl 3-methyl-2-[2-chlorosulfinyl-4-oxo-3-(α-benzhydryloxyphenylacetamido)-1-azetidinyl]-3-butenoate;

p-nitrobenzyl 3-methyl-2-[2-chlorosulfinyl-4-oxo-3-(α-benzyloxycarbonylaminophenylacetamido)-1-azetidinyl]-3 -butenoate;

t-butyl 3-methyl-2-[2-chlorosulfinyl-4-oxo-3-(α-t-butyloxycarbonylaminophenylacetamido)-1-azetidinyl]-3-butenoate;

p-nitrobenzyl 3-methyl-2-[2-chlorosulfinyl-4-oxo-3-(2-thienyl-α-p-nitrobenzyloxycarbonylaminoacetamido)-1-azetidinyl]-3-butenoate;

p-nitrobenzyl 3-methyl-2-[2-chlorosulfinyl-4-oxo-3-(2'-thienylacetamido)-1-azetidinyl]-3-butenoate;

benzyl 3-methyl-2-[2-chlorosulfinyl-4-oxo-3-(3'-thienylacetamido)-1-azetidinyl]-3-butenoate;

p-methoxybenzyl 3-methyl-2-[2-chlorosulfinyl-4-oxo-3-phenylthioacetamido-1-azetidinyl]-3-butenoate;

benzhydryl 3-methyl-2-[2-chlorosulfinyl-4-oxo-3-(2',5'-dichlorophenylthioacetamido)-1-azetidinyl]-3-butenoate;

t-butyl 3-methyl-2-[2-chlorosulfinyl-4-oxo-3-(4'-chloroacetoxyphenylthioacetamido)-1-azetidinyl]-3-butenoate;

p-nitrobenzyl 3-methyl-2-[2-chlorosulfinyl-4-oxo-3-(3'-nitrophenylthioacetamido)-1-azetidinyl]-3-butenoate;

p-nitrobenzyl 3-methyl-2-[2-chlorosulfinyl-4-oxo-3-(2'-cyanophenylthioacetamido)-1-azetidinyl]-3-butenoate;

p-methoxybenzyl 3-methyl-2-[2-chlorosulfinyl-4-oxo-3-(4'-trifluoromethylphenylthioacetamido)-1-azetidinyl]-3-butenoate;

benzyl 3-methyl-2-[[3-chlorosulfinyl-4-oxo-3-[3'-(2''-chlorophenyl)-5'-methylisoxazol-4'-ylcarbamido]-1-azetidinyl] -3-butenoate;

acetoxymethyl 3-methyl-2-[2-chlorosulfinyl-4-oxo-3-(3'-methylphenylthioacetamido)-1-azetidinyl]-3butenoate;

2,2,2-trichloroethyl 3-methyl-2-[2-chlorosulfinyl-4-oxo-3-(4'-methoxyphenylthioacetamido)-1-azetidinyl]-3-butenoate;

p-nitrobenzyl 3-methyl-2-[2-chlorosulfinyl-4-oxo-3-(2',2'-dimethyl-3'-acetyl-5'-oxo-4'-phenylimidazolidin-1'-yl)-1-azetidinyl]-3-butenoate;

benzyl 3-methyl-2-[2-chlorosulfinyl-4-oxo-3-((2',2'-dimethyl-3'-nitroso-3'-5'-oxo-4'-(4'''-formyloxyphenyl)-imidazolidin-1'-yl))-1-azetidinyl]-3-butenoate; and the like.

As hereinbefore noted, the sulfinyl chlorides produced by the process of this invention are useful as intermediates and can be ring-closed to the corresponding 3-exomethylenecepham sulfoxides by subjection of the sulfinyl chloride to a Friedel-Crafts catalyst, for example, stannic chloride.

The cyclization generally is carried out in the presence of a dry inert organic solvent. Any of a wide variety of dry inert organic solvents may be employed as the medium for the cyclization reaction. By "inert organic solvent" is meant an organic solvent which, under the conditions of cyclization, does not appreciably react either with the reactants or the products. Since the sulfinyl chloride starting material, like other acid chloride reagents, is susceptible to hydrolysis and to attack by other protic compounds, e.g. alcohols and amines, moisture and other such protic compounds should be excluded from the reaction medium. A dry aprotic organic solvent thus is preferred. Trace amounts of water, such as may be present in commercially dried solvents, can be tolerated; however, it is preferred that cyclization be carried out under anhydrous conditions. Suitable solvents include, for example, aromatic hydrocarbons, such as, benzene, toluene, xylene, chlorobenzene nitrobenzene, nitromesitylene and the like; halogenated aliphatic hydrocarbons, such as chloroform, methylene chloride, carbon tetrachloride, 1,2-dichloroethane (ethylene chloride), 1,1,2-trichloroethane, 1,1-dibromo-2-chloroethane; and other solvents recognized by those skilled in the art as suitable for Friedel-Crafts type reactions, including, among others, carbon disulfide and nitromethane. Preferred solvents are aromatic hydrocarbons, particularly benzene and toluene, and halogenated aliphatic hydrocarbons, particularly methylene chloride and ethylene chloride.

Cyclization of the azetidinone sulfinyl chloride is carried out at a temperature ranging from about 10° C. to about 115° C., and preferably, between about 20° C. and 90° C. The optimum temperature of cyclization is determined by the particular Friedel-Crafts catalyst which is employed. For example, when stannic chloride is employed, cyclization proceeds at room temperature, whereas, when other Friedel-Crafts catalysts are employed, higher temperatures may be required.

In order to ensure completion of the cyclization reaction, at least one equivalent of the Friedel-Crafts catalyst is employed for each of the sulfinyl chloride starting material. Using less than one equivalent of the Friedel-Crafts catalyst reagent may result in a lower conversion of product and thus may leave a portion of the sulfinyl chloride unreacted. Typically, the amount of Friedel-Crafts catalyst reagent employed will range from slightly over one equivalent to about two equivalents per mole of the sulfinyl chloride. Preferably about 1.1 equivalents of the catalyst reagent is employed per mole of the sulfinyl chloride.

The time of the reaction generally will range from about 15 minutes to about 2 hours, the reaction time being dependent to some extent upon the particular reactants, the solvents employed, and the temperature at which the reaction is carried out. Usually, the reaction will be completed after the reactants have been maintained in contact at the preferred temperature for about 45 to about 90 minutes. The reaction mixture can easily be monitored, for example, by comparative thin-layer chromatography, to determine when the cyclization reaction has reached completion.

The 3-exomethylenecepham sulfoxides produced by cyclization of the sulfinyl chlorides of this invention can be isolated and purified by employing conventional experimental techniques. These include chromatographic separation, filtration, crystallization, recrystallization and like methods.

The 3-exomethylenecepham sulfoxide cyclization products are useful as intermediates in the preparation of antibiotic compounds. The sulfoxides can be reduced by known procedures, typically with phosphorous trichloride or phosphorous tribromide in dimethylformamide, to provide the corresponding 3-exomethylenecephams.

The exomethylenecephams can be employed in the preparation of novel cephem antibiotics of the formula

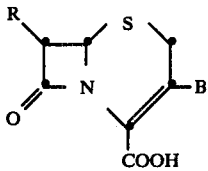

in which B is, for example, chloro, bromo or methoxy. Such chemical conversions of 3-exomethylenecepham compounds have been disclosed in the chemical literature [Robert R. Chauvette and Pamela A. Pennington, *Journal of the American Chemical Society*, 96, 4986 (1974)].

In general, the 3-exomethylenecepham compounds are converted by low temperature ozonolysis to 3-hydroxycephems which, in turn, can be treated with diazomethane at room temperature in tetrahydrofuran containing 1 equivalent of triethylamine to afford the 3-methoxycephem derivatives. The 3-halocephems are derived from the 3-hydroxycephem esters by treatment with a halogenating reagent such as thionyl chloride or phosphorus tribromide in N,N-dimethylformamide.

The corresponding cephem acids exhibit potent antibacterial activity. These are available by cleavage of the ester function. Deesterification can be achieved, depending on the nature of the protecting group, by any of several recognized procedures, including (1) treatment with an acid such as trifluoroacetic acid, formic acid, hydrochloric acid or the like; (2) treatment with zinc and an acid such as formic acid, acetic acid or hydrochloric acid; or (3) hydrogenation in the presence of palladium, platinum, rhodium or a compound thereof, in suspension, or on a carrier such as barium sulfate, carbon, alumina or the like.

This invention is further illustrated by reference to the examples which follow. It is not intended that this invention be limited in scope by reason of any of the examples provided herein.

EXAMPLE 1

Preparation of Methyl 3-Methyl-2-(2-chlorosulfinyl-4-oxo-3-phthalimido-1-azetidinyl)-3-butenoate A solution of 18.8 g. (50 mmol) of methyl 6$\beta$-phthalimido-2,2-dimethylpenam-3-carboxylate-1-oxide and 6.7 g. (50 mmol) of N-chlorosuccinimide in 1000 ml. of dry carbon tetrachloride was refluxed for 70 minutes. The mixture was cooled and then was washed with water and brine. After drying over MgSO$_4$, the solvent was evaporated, and 19.5 g. (95%) of the title compound as a colorless solid was obtained. The nmr spectrum (CDCl$_3$) indicates that the product is the sulfinyl chloride.

nmr (CDCl$_3$) $\delta$ 1.97 (broad s, 3), 3.86 (s, 3), 5.05 (br. s, 2), 5.2 (d, 1, J=2 Hz), 5.77 (d, 1, J=4 Hz), 5.9 (d, 1, J=4 Hz), and 7.83 (m, 4).

EXAMPLE 2

Preparation of Methyl 7-phthalimido-3-methylene-cepham-4-carboxylate-1-oxide

The product from Example 1 was dissolved in 1 L. of dry CH$_2$Cl$_2$, and 6 ml. (50 mmol) of anhydrous stannic chloride were added. The resulting solution was stirred for 45 minutes, washed with 1N hydrochloric acid (2×200 ml.) and dried over MgSO$_4$. Evaporation in vacuo gave a light yellow foam (18.4 g., 98.4%) composed of a mixture of the R and S sulfoxide isomers (ca. 3:2 nmr).

A portion (1.26 g.) of this mixture was separated by chromatography over silica gel using chloroform/ethyl acetate as solvent. Fractions 6–10 contained pure R-sulfoxide (340 mg.). The R-sulfoxide was recrystallized from methylene chloride/cyclohexane, mp 201°–202°; nmr (CDCl$_3$) $\delta$ 3.62 and 4.12 (ABq, 2, J=14 Hz), 3.85 (s, 3), 4.88 (d, 1, J=4.5 Hz), 5.25 (br. s, 1), 5.58 (m, 2), 5.97 (d, 1, J=4.5 Hz), and 7.84 (m, 4); mass spec., m/e 374, 358, 346, 298, 287, 239, 220; ir (KBr): 1780, 1745, 1390, 1345, 1192, 1051, 920, 730 cm$^{-1}$.

Anal. Calcd for C$_{17}$H$_{14}$N$_2$O$_6$S (374.37): C, 54.54; H, 3.77; N, 7.48; O, 25.64; S, 8.56. Found: C, 54.41; H, 4.06; N, 7.26; O, 25.59; S, 8.41.

Fractions 11–18 contained a mixture of the R- and S-sulfoxides, and fractions 19–35 gave 210 mg. of the S-sulfoxide, which was recrystallized from methylene chloride/cyclohexane; nmr (CDCl$_3$) $\delta$ 3.63 (s, 2), 3.82 (s, 3), 4.90 (d, 1, J=4.5 Hz), 5.32 (s, 1), 5.46 (br. s, 1), 5.64 (d, 1, J=4.5 Hz), 5.77 (s, 1), and 7.84 (m, 4); mass spec., m/e 374, 358, 346, 298, 239, 220; ir (KBr): 1775, 1745, 1725, 1390, 1205, 1111, 1051, 730, 715 cm$^{-1}$.

Anal. Calcd for C$_{17}$H$_{14}$N$_2$O$_6$S: C, 54.54; H, 3.77; N, 7.48. Found: C, 54.33; H, 3.76; N, 7.36.

EXAMPLE 3

Preparation of p-Nitrobenzyl 3-Methyl-2-(2-chlorosulfinyl-4-oxo-3-phthalimido-1-azetidinyl)-3-butenoate A solution of 49.7 g. (0.1 mol) p-nitrobenzyl 6$\beta$-phthalimido-2,2-dimethylpenam-3-carboxylate-1-oxide and 13.4 g. (0.1 mol.) of N-chlorosuccinimide in 1.5 L. of 1,2-dichloroethane was refluxed for 70 minutes. The mixture was cooled, washed with water and brine, and then dried over MgSO$_4$. The solvent then was evaporated, and the residue was dried in vacuo for 3 hours to obtain 52.0 g. of the title compound.

nmr (CDCl$_3$) $\delta$ 1.97 (s, 3), 5.05 (s, 1), 5.4 (s, 2), 5.76 (d, 1, J=5 Hz), 5.91 (d, 1, J=5 Hz), 7.83 (m, 8 Ar H's).

EXAMPLE 4

Preparation of p-Nitrobenzyl 7-Phthalimido-3-methylenecepham-4-carboxylate-1-oxide To a solution of 23.1 g. of p-nitrobenzyl 3-methyl-2-(2-chlorosulfinyl-4-oxo-3-phthalimido-1-azetidinyl)-3-butenoate in 400 ml. of dichloromethane, 6.1 ml. of anhydrous stannic chloride were added. The mixture was stirred at room temperature. A precipitate formed and increased in amount as the reaction time progressed. After 45 minutes the reaction mixture was washed with 1N sulfuric acid, water, sodium bicarbonate solution, and brine. The organic layer then was dried, and the solvent was evaporated to obtain 16.72 g. (78%) of product shown by nmr spectrum to be a mixture of the R- and S-sulfoxides. The isomers were separated by fractional recrystallization from acetone and dichloromethane.

The R-sulfoxide was obtained as colorless prisms which softened at 155° C. and melted completely at 213° C.; ir (CHCl$_3$) 1790, 1780, 1738 and 1723 cm$^{-1}$; mass spec. m/e: 495, 279, 367, 343; nmr (CDCl$_3$) δ 3.58 and 4.10 (ABq, 2, J=13 Hz), 4.87 (d, 1, J=4.5 Hz), 5.33 (s, 2+1), 5.57 (m, 2), 5.95 (d, 1, J=4.5 Hz), 7.4–8.4 (m, 8, Ar H).

Anal. Calcd for C$_{23}$H$_{17}$N$_3$O$_8$S (495.5): C, 55.76; H, 3.46; N, 8.48; O, 25.83; S, 6.47. Found: C, 55.50; H, 3.45; N, 8.65; O, 25.17; S, 6.32.

The S-sulfoxide was obtained as colorless prisms, mp 190°–192° C.; ir (mull) 1780, 1775, 1741 and 1728 cm$^{-1}$; nmr (CDCl$_3$) δ 3.5 and 3.7 (ABq, 2, J=15 Hz), 4.9 (d, 1, J=4.5 Hz), 5.34 (s, 2), 5.46 (m, 2), 5.6 (d, 1, J=4.5 Hz), 5.8 (s, 1), 7.4–8.4 (m, 8).

Anal. Calcd for C$_{23}$H$_{17}$N$_3$O$_8$S: C, 55.76; H, 3.46; N, 8.48; O, 25.83; S, 6.47. Found: C, 55.58; H, 3.62; N, 8.25; O, 25.19; S, 6.18.

EXAMPLE 5

Preparation of p-Nitrobenzyl 3-Methyl-2-(2-chlorosulfinyl-4-oxo-3-phenoxyacetamido-1-azetidinyl)-3-butenoate A solution of 500 mg. (1 mmol.) of p-nitrobenzyl 6β-phenoxyacetamido-2,2-dimethylpenam-3-carboxylate-1-oxide and 134 mg. (1 mmol.) of N-chlorosuccinimide in 40 ml. of well dried 1,1,2-trichloroethane was refluxed for 90 minutes. The mixture was cooled, washed with water and brine, dried, and the solvent evaporated in vacuo. According to the nmr spectrum the title compound was obtained in nearly quantitative yield.

nmr (CDCl$_3$) δ 1.91 (broad s, 3), 4.53 (s, 2), 5.05 (broad s, 1), 5.23 (m, 2), 5.33 (s, 2), 5.57 (d, 1, J=4.5 Hz), 6.18 (dd, 1, J=4.5 Hz) and 6.9–8.1 (m, 9, Ar H).

EXAMPLE 6

Preparation of p-Nitrobenzyl 3-methyl-2-(2-chlorosulfinyl-4-oxo-3-phenoxyacetamido-1-azetidinyl)-3-butenoate A mixture of 6.0 g. (12 mmol) of p-nitrobenzyl 6-phenoxyacetamido-2,2-dimethylpenam-3-carboxylate-1-oxide in 500 ml. of dry toluene was refluxed for 10 minutes using a Dean-Stark trap to remove traces of water. Upon completion of the drying step 1.8 g. of N-chlorosuccinimide were added, and the mixture was refluxed for 90 minutes. The mixture then was cooled to about 50° C. and evaporated to obtain the sulfinyl chloride product.

EXAMPLE 7

Preparation of p-Nitrobenzyl 7-Phenoxyacetamido-3-methylenecepham-4-carboxylate-1-oxide To the sulfinyl chloride obtained from Example 6 and dissolved in dry toluene were added 1.8 ml. of anhydrous stannic chloride. The mixture was stirred at room temperature for 90 minutes. To the mixture then were added 100 ml. of water and 100 ml. of ethyl acetate. The layers were separated, and the organic layer was washed with 1N HCl, NaHCO$_3$ solution, and brine, and dried over MgSO$_4$. The solvent then was evaporated to dryness. To the residue 10 ml. of ethyl acetate were added, and crystals immediately began to separate. The product, 2.16 g (36%), was collected. A sample was recrystallized from ethyl acetate and acetone to obtain large prisms, m.p. 200–201° C. nmr (CDCl$_3$) δ 3.5 and 3.75 (ABq, 2, J=15 Hz), 4.55 (s, 2), 4.83 (d, 1, J=4.5 Hz), 5.3 (s, 2), 5.33 (s, 1), 5.5 (s, 1), 5.78 (s, 1), 5.94 and 6.1 (ABq, 1, J=4.5 Hz), 6.9–8.3 (m, 9).

Anal. Calcd for C$_{23}$H$_{21}$N$_3$O$_8$S (499.5):
C, 55.31; H, 4.24; N, 8.41; O, 25.62; S, 6.42.
Found C, 55.06; H, 4.14; N, 8.30; O, 25.62; S, 6.26.

EXAMPLE 8

Preparation of p-Nitrobenzyl 3-Methyl-2-(2-chlorosulfinyl-4-oxo-3-formamido-1-azetidinyl)-3-butenoate.

A solution of 1.43 g. of p-nitrobenzyl 6β-formamido-2,2-dimethylpenam-3-carboxylate-1-oxide and 500 mg. of N-chlorosuccinimide in 40 ml. of dry 1,1,2-trichloroethane was refluxed for 90 minutes. The mixture was cooled, washed with water and brine, dried over MgSO$_4$, and the solvent was evaporated. The nmr spectrum indicates conversion to the title compound.

nmr (CDCl$_3$) δ 1.91 (broad s, 3), 5.03 (broad s, 1), 5.20 (m, 2), 5.34 (s, 2), 5.62 (d, 1, J=4.5 Hz), 6.12 and 6.3 (ABq, 1, J=4.5 Hz), and 7.4–8.4 (m, 4, Ar H's).

EXAMPLE 9

Preparation of 2,2,2-Trichlorethyl 3-Methyl-2-(2-chlorosulfinyl-4-oxo-3-phenylacetamido-1-azetidinyl)-3-butenoate.

A solution of 500 mg. of 2,2,2-trichloroethyl 6β-phenylacetamido-2,2-dimethylpenam-3-carboxylate-1-oxide and 134 mg. of N-chlorosuccinimide in 40 ml. of dry toluene was refluxed for 90 minutes. The mixture was cooled, washed with H$_2$O and brine, dried over MgSO$_4$, and the solvent was evaporated on a rotavapor. The title compound was recovered as a colorless foam.

nmr (CDCl$_3$ δ δ1.90 (s, 3), 3.55 (s, 2), 4.8 (m, 2), 4.95 (d, 1, J=4.5 Hz), 5.03–5.21 (m, 3), 5.65 and 5.70 (ABq, 1, J=4.5 Hz), 7.3 (s, 5) and 7.5 (d, NH, J=10Hz).

EXAMPLE 10

Preparation of 2,2,2-Trichloroethyl 7-Phenylacetamido-3-methylenecepham-4-carboxylate-1-oxide To the sulfinyl chloride of Example 9 were added 0.28 ml. of anhydrous stannic chloride. The mixture was stirred for 90 minutes. The mixture then was washed with water and brine, and the solvent was evaporated. The residue was crystallized from a mixture of ethyl acetate and ether. The nmr spectrum of the collected prisms was in agreement with the structure of the title compound; nmr (CDCl$_3$) δ 3.5 and 3.81 (ABq, 2, J=14 Hz), 3.53 (s, 2), 4.8 (m, 2), 4.9 (d, 1, J=4.5 Hz), 5.37 (s, 1), 5.5 (s, 1), 5.82 (s, 1), 5.9 and 6.07 (ABq, 1, J=4.5 Hz), 7.0 (d, NH, J=10 Hz), 7.33 (s, 5).

EXAMPLE 11

Preparation of Methyl 3-Methyl-2-[2-chlorosulfinyl-4-oxo-3-(2',2'-dimethyl-3'-nitroso-5'-oxo-4'-phenylimidazolidin-1'-yl)-1-azetidinyl]-3-butenoate To 55 ml. of dry benzene which had been further dried by azeotrope removal of moisture were added 0.896 g. (2 mmol) of methyl 6-(2,2-dimethyl-3-nitroso-5-oxo-4-phenylimidazolidin-1-yl)-2,2-dimethylpenam-3-carboxylate-1-oxide and 0.536 g. (4 mmol) of N-chlorosuccinimide. The mixture was purged with nitrogen and refluxed for about 1 hour. The resulting reaction mixture was a solution, pale greenish-yellow in color. The mixture was cooled, and the solvent of a portion of the mixture was evaporated in vacuo to obtain the product as a residue. An nmr analysis of the residue indicated the presence of the sulfinyl chloride product.

EXAMPLE 12

Preparation of Methyl 7-(2',2'-Dimethyl-3'-nitroso-5'-oxo-4'-phenylimidazolidin-1'-yl)-3-methylene-cepham-4-carboxylate-1-oxide The remainder of the reaction mixture from Example 11 was cooled rapidly in an ice bath under nitrogen, and 0.33 ml. of stannic chloride was added. A light orange precipitate formed immediately. The mixture was stirred for 135 minutes, and 55 ml. each of N,N-dimethylacetamide and ethyl acetate were added. The mixture, a pale greenish-yellow solution, was extracted with 60 ml. of water and then with 60 ml. of saturated sodium chloride solution. The organic layer was dried over calcium sulfate, and the solvent was evaporated to 1.3 g. of a yellow oil. The yellow oil was dissolved in dichloromethane, and the solution was placed on four preparative TLC plates. The plates were developed with a 1:1 mixture of benzene and ethyl acetate. Two bands of material were noted. The title compound, represented by one of the bands, was collected with acetonitrile. The nmr spectrum of the product is consistent for the structure of the title compound.

nmr (CDCl$_3$) $\delta$2.07 (s, 6, gem-dimethyl), 3.73 (s, 3, COOCH$_3$), 4.7–5.6 (m), and 7.3 (s, ArH).

EXAMPLE 13

Preparation of Methyl 3-Methyl-2-(2-chlorosulfinyl-4-oxo-3-phthalimido-1-azetidinyl)-3-butenoate To 300 ml of carbon tetrachloride were added 3.7 g. (10 mmole) of methyl 6-phthalimido-2,2-dimethylpenam-3-carboxylate-1-oxide and 2.2 g. (10 mmol.) of N-chloro-N-methyl-p-toluenesulfonamide. The mixture was heated at reflux for 90 minutes. The reaction mixture then was cooled to room temperature, washed with water and brine, dried over magnesium sulfate, and divided into two equal portions.

The first portion was evaporated to dryness in vacuo to obtain, as a residue the title compound, the structure of which was verified by nmr analysis.

nmr (CDCl$_3$) $\delta$2.0 (s, 3, allylic CH$_3$), 3.84 (s, 3, CH$_3$ ester), 5.1 (s, 2, vinylic CH$_2$), 5.2 (s, 1, C$_4$-H), and 5.6–6.0 (m, 2, C$_6$-H and C$_7$-H).

EXAMPLE 14

Preparation of Methyl 7-Phthalimido-3-methylenecepham-4-carboxylate-1-oxide

To the remaining portion of the reaction mixture from Example 13 were added 1.43 g. (5 mmol.) of stannic chloride. The mixture was stirred at room temperature for two hours. The solvent then was evaporated in vacuo. The resulting residue was redissolved in ethyl acetate, and the ethyl acetate solution was successively washed with water, 5 percent HCl, 5 percent sodium bicarbonate, and brine. The ethyl acetate solution then was dried over magnesium sulfate and evaporated to dryness in vacuo. The resulting residue (about 1.1 g.) was triturated with ether. The nmr (CDCl$_3$) spectrum of the recovered product was consistent with the structure of the title compound.

EXAMPLE 15

Preparation of Methyl 7-Phthalimido-3-methylenecepham-4-carboxylate

About one-half of the crude product from Example 14 was dissolved in 25 ml. of cold N,N-dimethylformamide. The solution was treated with 345 mg. (2.5 mmol.) of phosphorous trichloride, and the mixture was stirred in an ice bath for 30 minutes. The resulting reaction mixture then was poured into a mixture of water and ethyl acetate. The ethyl acetate solution was separated, washed with 5 percent hydrochloric acid and water, dried over magnesium sulfate and evaporated to dryness in vacuo. The nmr spectrum of the residue which was obtained was consistent with the structure of the title compound.

nmr (CDCl$_3$) $\delta$3.4 (ABq, 2, C$_2$-H$_2$), 3.8 (s, 3, CH$_3$ ester), 5.29–5.6 (m, 5, C$_3$-CH$_2$, C$_4$-H, C$_6$-H, C$_7$-H).

EXAMPLE 16

Preparation of p-Nitrobenzyl 3-Methyl-2-(2-chlorosulfinyl-4-oxo-3-phenoxyacetamido-1-azetidinyl)-3-butenoate To 150 ml. of distilled and molecular sieve-dried toluene were added 3.0 g. (6 mmol.) of p-nitrobenzyl 6-phenoxyacetamido-2,2-dimethylpenam-3-carboxylate-1-oxide and 1.3 g. (6 mmol.) of N-chloro-N-methyl-p-toluenesulfonamide. The mixture was heated at reflux for 60 minutes. The resulting reaction mixture then was cooled to room temperature. An aliquot (15 ml.) was separated, washed with water, and brine, dried over magnesium sulfate, and evaporated to dryness in vacuo. The nmr spectrum of the residue was consistent for the title compound contaminated with some N-methyl-p-toluenesulfonamide.

nmr (CDCl$_3$) $\delta$1.88 (s, 3, allylic CH$_3$), 5.0 (s, 2, vinylic CH$_2$), and 5.12 (s, 1, allylic H).

EXAMPLE 17

Preparation of p-Nitrobenzyl 7-Phenoxyacetamido-3-methylenecepham-4-carboxylate-1-oxide To the remainder of the reaction mixture from Example 16 were added 1.4 g. (5.4 mmol.) of stannic chloride. The mixture was stirred at room temperature for two hours. The resulting mixture then was successively washed with water, 5 percent hydrochloric acid, 5 percent sodium bicarbonate and brine. The mixture then was dried over magnesium sulfate and evaporated to dryness in vacuo. The nmr spectrum of the residue (700 mg.), after trituration with ether to remove N-methyl-p-toluenesulfonamide was consistent with the structure of the title compound.

nmr (CDCl$_3$) δ3.67 (ABq, 2, C$_2$-H$_2$), 4.5 (s, 2, α-CH$_2$), 4.94 (d, 1, C$_6$-H), 5.30–5.38 (2s, 4, C$_3$-CH$_2$ and ester CH$_2$), 5.79 (s, 1, C$_4$-H), and 6.02 (q, 1, C$_7$-H).

EXAMPLE 18

Preparation of p-Nitrobenzyl 7-Phenoxyacetamido-3-methylenecepham-4-carboxylate

About one-half of the product from Example 17 was dissolved in 25 ml. of dry N,N-dimethylformamide. The mixture was cooled in an ice bath, and 370 mg. (2.7 mmol.) of phosphorous trichloride were added. The mixture was stirred with cooling for 30 minutes. The mixture then was poured into a mixture of water and ethyl acetate. The ethyl acetate solution was separated, washed successively with 5 percent hydrochloric acid and brine, dried over magnesium sulfate, and evaporated to dryness in vacuo. The residue (350 mg.) was consistent by nmr analysis with the structure of the title compound.

nmr (CDCl$_3$) δ3.42 (ABq, 2, C$_2$-H$_2$), 4.56 (s, 2, α-CH$_2$), 5.2–5.5 (m, 6, C$_6$-H, C$_3$-CH$_2$, ester CH$_2$, and C$_4$-H), and 5.73 (q, 1, C$_7$-H).

EXAMPLE 19

Preparation of p-Nitrobenzyl 3-Methyl-2-(2-chlorosulfinyl-4-oxo-3-phenoxyacetamido-1-azetidinyl)-3-butenoate.

Tolune (425 ml.) was heated in equipment containing a Dean-Stark water trap to azeotropically remove any moisture which may be present, and 25 ml. of toluene were removed thereby. To the remaining toluene were added 10.0 g. (20 mmol.) of p-nitrobenzyl 6-phenoxyacetamido-2,2-dimethylpenam-3-carboxylate-1-oxide, the toluene being maintained at a temperature slightly below reflux. Toluene (200 ml.) was separately distilled, and 4.0 g. (22 mmol.) of N-chlorophthalimide were added. The resulting solution (warm) was added dropwise to the solution of the penicillin sulfoxide ester over a period of 30 minutes. The mixture remained a light yellow solution throughout addition. The mixture then was refluxed for 55 minutes after which time a sample was removed, and nmr (CDCl$_3$) analysis of the sample indicated virtually entire conversion of the penicillin sulfoxide ester to the title compound.

EXAMPLE 20

Preparation of p-Nitrobenzyl 7-Phenoxyacetamido-3-methylenecepham-4-carboxylate-1-oxide.

To 50 ml. of toluene were added 1.0 g. (2 mmol.) of p-nitrobenzyl 6-phenoxyacetamido-2,2-dimethylpenam-3-carboxylate-1-oxide and 0.3 ml. of ethyl N,N-dichlorocarbamate. The mixture was refluxed for 60 minutes, cooled, washed with water and brine, dried over magnesium sulfate, and evaporated to about 20 ml. of toluene.

The resulting residual toluene mixture was cooled and 0.25 ml. of stannic chloride was added. The mixture was stirred for 90 minutes and worked up in a manner in accordance with Example 7 to obtain 390 mg. of the title compound.

EXAMPLE 21

Preparation of Benzhydryl 3-Methyl-2-(2-chlorosulfinyl-4-oxo-3-phenoxyacetamido-1-azetidinyl)-3-butenoate.

To 800 ml. of dried toluene were added 20 gms. of benzhydryl 6-phenoxyacetamido-2,2-dimethylpenam-3-carboxylate-1-oxide. The mixture was refluxed in a system containing a Dean-stark water trap to axeotropically remove any moisture which may be present, and 100 ml. of toluene were removed thereby. To the mixture then were added 13.2 gms. of N-chlorosuccinimide. Refluxing was continued for 1.5 hours. The product was analyzed by nmr analysis which was consistent with the structure of the title compound.

nmr (CDCl$_3$) δ 1.88 (s, 3), 4.53 (s, 2), 4.90 (s, 1), 5.14 (s, 2), 5.54 (s, 1, J=4 Hz), 6.24 (q, 1, J=4Hz and 8 Hz), 6.95 (s, 1), 7.15-7.4 (m, 15), and 8.0 (d, 1, J=8 Hz).

EXAMPLE 22

Preparation of p-Nitrobenzyl 3-Mehyl-2-(2-chlorosulfinyl-4oxo-3-acetamido-1-azetidinyl)-3-butenoate Toluene (500 ml.) was heated in equipment containing a Dean-Stark water trap to azeotropically remove any moisture which may be present. To the resulting dried toluene was added 1.0 gms. (2.4 mmol.) of p-nitrobenzyl 6-azetamido-2,2-dimethylpenam-3-carboxylate-1-oxide. The resulting mixture was refluxed again using a Dean-Stark water trap to remove any additional amounts of water which may be present. The mixture then was cooled, and 400 mg. (2.9 mmol) of N-chlorosuccinimide were added. The mixture then was refluxed for 1 hour. A sample of the reaction mixture was withdrawn, and the solvent was removed. The product which was obtain was consistent by nmr analysis with the structure of the title compound.

nmr (CDCl$_3$) δ 1.86 (br. s, 3), 2.04, 2.09 (2s, 3), 4.80 (m, 1), 5.2 (m, 2), 5.28 (s, 2), 5.63 (m, 1), 6.05 (d, 1, J=4 Hz), and 7.4–8.4 (q, 4, ArH).

EXAMPLE 23

Preparation of p-Nitrobenzyl 7-Acetamido-3-methylenecepham-4-carboxylate-1-oxide The reaction mixture from Example 22 was cooled in an ice bath, and 1 ml. of stannic chloride was added. The mixture was maintained for two hours after which it was evaporated in vacuo to dryness. The resulting residue was dissolved in ethyl acetate, and the ethyl acetate mixture was washed once with a mixture of HCl, and aqueous sodium chloride and twice with aqueous sodium chloride, dried over magnesium sulfate, and evaporated in vacuo to dryness. The residue was dissolved in a minimum of ethyl acetate, and, after standing overnight, crystals of the title compound formed and were collected.

nmr (CDCl$_3$) δ 1.92 (s, 3), 3.80 (br. s, 2), 5.00 (d, 1, J=4 Hz), 5.32 (s, 2), 5.45–5.80 (m, 5), 7.60 (d, 2, J=8 Hz), 7.86 (d, 1, J=9 Hz), and 8.20 (d, 2, J=8 Hz).

EXAMPLE 24

Preparation of 2,2,2-Trichloroethyl 3-Methyl-2-[2-chlorosulfinyl-4-oxo-3-(4'-nitrobenzyloxycarbamido)-1-azetidinyl]-3-butenoate A mixture of 300 ml. of 1,1,2-trichloroethane and 10.26 gms. of 2,2,2-trichloroethyl 6-(4'-nitrobenzyloxycarbamido)-2,2-dimethylpenam-3-carboxylate-1-oxide was prepared. The mixture was refluxed with removal of about 75 ml. of the solvent to promote drying of the reaction medium. The mixture then was cooled, and propylene oxide was added followed by 4 gms. of N-chlorosuccinimide. The temperature of the mixture was raised to 102° C., and the mixture was refluxed for 2.5 hours. A sample of the reaction mixture was removed, the solvent was evaporated, and an nmr analysis of the residue was consistent with the structure of the title compound.

nmr (CDCl$_3$) δ 1.94 (br. s, 3), 4.83 (s, 2), 5.25 (s, 2), 5.0–5.4 (m, 3), 6.20 (d, 1, J=4 Hz), 7.55 (d, 2, J=8 Hz), and 8.24 (d, 2, J=9 Hz).

EXAMPLE 25

Preparation of 2,2,2-Trichloroethyl 7-(4'-Nitrobenzyloxycarbamido)-3-methylcephem-4-carboxylate-1-oxide A portion representing about one-third of the reaction mixture from Example 24 was evaporated, and the residue was dissolved in 100 ml. of dried methylene chloride. To the resulting mixture was added 5 ml. of stannic chloride. The mixture was treated in accordance with the method of Example 23 to obtain 700 mg. of the title compound.

nmr (CDCl$_3$) δ 3.60, 3.88 (ABq, 2, J=15 Hz), 4.82 (s, 2), 4.94 (d, 1, J=4.5 Hz), 5.23 (s, 2), 5.40 (s, 1), 5.56 (s, 1), 5.83 (s, 1), 6.37 (d, 1, J=10 Hz), 7.46 (d, 2, J=9 Hz), and 9.20 (d, 2, J=9 Hz).

EXAMPLE 26

Preparation of p-Nitrobenzyl 3-Methyl-2-[2-chlorosulfinyl-4-oxo-3-((N-phenoxyacetyl)-N-(2',2',2'-trichloroethoxycarbonyl)amino))-1-azetidinyl]-3-butenoate A mixture of 4.855 gms. (10 mmol.) of p-nitrobenzyl 6-phenoxyacetamido-2,2-dimethylpenam-3-carboxylate, 16.94 gms. (80 mmol.) of 2,2,2-trichloroethyl chloroformate, 18 ml. of N,O-(bis-trimethylsilyl)trifluoromethylacetamide, and 20 ml. of methylene chloride was prepared. The mixture was permitted to stand at room temperature overnight. The mixture then was heated at reflux for 7 hours after which it was again permitted to stand at room temperature overnight. Heating then was continued for an additional 6 hours. The mixture then was evaporated to a residue, and the residue was dissolved in benzene which then was added to a large excess of heptane. The resulting insoluble material was filtered off, dissolved in benzene, and chromatographed over silica gel using a benzene-ethyl acetate elution gradient. p-Nitrobenzyl 6-[N-(phenoxyacetyl)-N-(2,2,2-trichloroethoxycarbonyl)amino]-2,2-dimethylpenam-3-carboxylate (4.76 gms.; 72 percent) was obtained as product.

nmr δ 1.41 (s, 3), 1.62 (s, 3), 4.61 (s, 1), 4.84 (d, 1, J=12 Hz), 4.99 (d, 1, J=12 Hz), 5.20 (s, 2), 5.30 (s, 2) 5.56 (s, 2), 6.8–7.4 (m, 5), 7.53 (s, 2, J=9 Hz), and 8.22 (d, 2, J=9 Hz).

To about 75 ml. of acetone were added 2.54 gms. (3.84 mmol.) of the above product. The mixture was cooled to −70° C., and an excess of oxone was admitted to the reaction mixture at approximately 1.17 mmol. per minute for nine minutes during which time the reaction mixture turned blue. The mixture was maintained at −70° C. for about 35 minutes after which it was warmed to room temperature and the solvent was removed in vacuo to obtain 2.76 gms. of p-nitrobenzyl 6-[N-(phenoxyacetyl)-N-(2,2,2-trichloroethoxycarbonyl)amino]-2,2-dimethylpenam-3-carboxylate-1-oxide.

nmr δ 1.22 (s, 3), 1.62 (s, 3), 4.60 (s, 1), 4.78 d, 1, J=5 Hz), 4.93 (s, 2), 5.26 (s, 2), 5.30 (s, 2), 5.93 (d, 1, J=5 Hz), 6.8–7.4 (m, 5), 7.51 (d, 2, J=9 Hz), and 8.20 (d, 2, J=9 Hz).

To 40 ml. of dry benzene were added 792 mg. (about one mmol.) of the above product and 155 mg. (about 1.2 mmol.) of N-chlorosuccinimide. The resulting mixture was heated at reflux for one hour, and nmr of the reaction mixture indicated the presence of the title compound.

nmr δ 1.92 (s, 3), 4.87 (s, 1), 4.96 (s, 2), 5.05 (s, 2), 5.23 (s, 2), 5.26 (s, 1), 5.34 (s, 2), 5.64 (d, 1, J=5 Hz), 5.95 (d, 1, J=5 Hz), 6.10 (d, 1, J=5 Hz), 6.8–7.5 (m, 5), 7.56 (d, 2, J=9 Hz), and 8.23 (d, 2, J=9 Hz).

EXAMPLE 27

Preparation of p-Nitrobenzyl 7-[N-(phenoxyacetyl)-N-(2,2,2-trichloroethoxycarbonyl)amino]-3-methylenecepham-4-carboxylate-1-oxide To the reaction mixture from Example 26 cooled to room temperature were added 390 mg. (1.5 mmol.) of stannic chloride. The mixture was maintained at room temperature for 75 minutes, and 5 ml. of methanol then were added. Additional benzene was added, and the resulting mixture was washed three times with a mixture of HCl and aqueous sodium chloride. The benzene layer was dried over sodium sulfate and evaporated in vacuo to dryness. The residue was chromatographed over silica gel (15% water) with a benzene-ethyl acetate gradient to obtain 246 mg. of the title compound.

nmr δ 3.42 (d, 1, J=13 Hz), 3.98 (d, 1, J=13 Hz), 4.64 (d, 1, J=5 Hz), 4.94 (s, 2), 5.25 (s. 2), 5.30 (s, 2), 5.34 (s, 1), 5.47 (s, 1), 6.04 (d, 1, J=5 Hz), 6.8–7.4 (m, 5), 7.55 (d, 2, J=9 Hz), and 8.23 (d, 2, J=9 Hz).

EXAMPLE 28

Preparation of 2,2,2-Trichloroethyl 3-methyl-2-[2-chlorosulfinyl-4-oxo-3-(α-t-butyloxycarbonylaminophenylacetamido)-1-azetidinyl]-3-butenoate A solution of 2.85 g. (5 mmol) of 2,2,2-trichloroethyl 6-(α-t-butyloxycarbonylaminophenylacetamido)-2,2-dimethylpenam-3-carboxylate-1-oxide in 175 ml. of toluene was dried azeotropically by distillation of about 50 ml. of toluene from the mixture. To the dried solution was added 0.685 g. (5.5 mmol.) of N-chlorosuccinimide. The resulting mixture was refluxed for 70 minutes. The mixture was allowed to cool to room temperature and then was filtered and evaporated in vacuo to dryness to provide the title product (contaminated with succinimide).

nmr (CDCl$_3$) δ 1.40 (s, 9, tert-butyl), 1.95 (s, 3, CH(CH$_3$)=CH$_2$) 4.82 (broad s, 2, ester CH$_2$), 5.20 (m, 3, CH(CH$_3$)=CH$_2$ and CHCOOCH$_2$CCl$_3$), 5.38 (d, 1, J=4.5 Hz, azetidinone C$_2$-H), 5.80 (m, 1, azetidinone C$_3$-H) and 7.34 (s, 5, ArH).

EXAMPLE 29

Preparation of 2,2,2-Trichloroethyl 3-methyl-2-[2-chlorosulfinyl-4-oxo-3-(2-thienylacetamido)-1-azetidinyl]-3-butenoate A solution of 3.5 g. of 2,2,2-trichloroethyl 6-(2-thienylacetamido)-2,2-dimethylpenam-3-carboxylate 1-oxide in 350 ml. of toluene was prepared and dried azeotropically by distilling 100 ml. of toluene from the mixture. The mixture was cooled, and 1 g. of N-chlorosuccinimide was added. The resulting mixture was then refluxed for 50 minutes, cooled, and filtered. A 5 ml. portion of the mixture was evaporated in vacuo to dryness to provide the title product.

nmr (CDCl$_3$) δ 1.87 (s, 3, CH(C$\underline{H}$$_3$)=CH$_2$), 3.82 (s, 2, side chain CH$_2$), 4.80 (ABq, 2, J=13 Hz, -C$\underline{H}$$_2$CCl$_3$), 5.18 (m, 3, -C$\underline{H}$(CH$_3$)=C$\underline{H}$$_2$), 5.50 (d, 1, J=4.5 Hz, azetidinone C$_2$-H), and 6.05 (m, 1, azetidinone C$_3$-H).

EXAMPLE 30

Preparation of 2,2,2-Trichloroethyl 7-(2-thienylacetamido)-3-methylenecepham-4-carboxylate-1-oxide To the remainder of the toluene solution of the sulfinyl chloride product from Example 29 were added 1.5 ml. of anhydrous stannic chloride. The mixture was allowed to stir for 1 hour. Ethyl acetate (250 ml.) was added, and the resulting solution was washed with three 400 ml. portions of brine, dried over anhydrous MgSO$_4$, and evaporated in vacuo to dryness. The product thereby obtained was dissolved in 30 ml. of ethyl acetate and 350 mg. of the title compound crystallized and were separated.

nmr (DMSO$_{d-6}$) δ 3.38 (broad s, 2, C$_2$-H), 3.80 (s, 2, side chain CH$_2$), 5.02 (s, 2, -C$\underline{H}$$_2$CCl$_3$), 5.04 (d, 1, J=4 Hz, C$_6$-H), 5.4–5.8 (m, 4), 6.8–7.4 (m, 3, thienyl), and 8.16 (d, 1, J=8 Hz, —N$\underline{H}$).

I claim:

1. A process for preparing a cis sulfinyl chloride of the formula

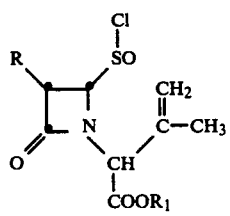

which comprises the step of reacting a penicillin sulfoxide of the formula

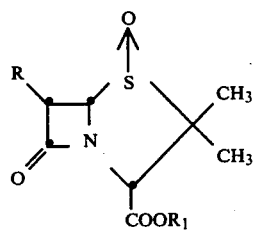

with an N-chloro halogenating agent at a temperature of from about 75° C. to about 135° C. in an inert solvent and under anhydrous conditions; in which, in the above formulae, R$_1$ is a carboxylic acid protecting group; and R is (1) an imido group of the formula

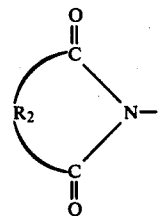

in which Rhd 2 is C$_2$-C$_4$ alkenylene or 1,2-phenylene;
(2) an amido group of the formula

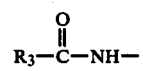

in which R$_3$ is
(a) hydrogen, C$_1$-C$_3$ alkyl, halomethyl, cyanomethyl benzyloxy, 4-nitrobenzyloxy, t-butyloxy, 2,2,2-trichloroethoxy, 4-methoxybenzyloxy, 3-(2-chlorophenyl)-5-methylisoxazol-4-yl;
(b) the group R' in which R' is phenyl or phenyl substituted with 1 or 2 halogens, protected hydroxy, nitro, cyano, trifluoromethyl, C$_1$-C$_4$ alkyl, or C$_1$-C$_4$ alkoxy;
(c) a group of the formula R"-(Q)$_m$-CH$_2$- in which R" is R' as defined above, 1,4-cyclohexadienyl, 2-thienyl, or 3-thienyl; m is 0 or 1; and Q is O or S; subject to the limitation that when m is 1, R" is R'; or
(d) a group of the formula

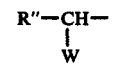

in which R"' is as defined above, and W is protected hydroxy or protected amino;
(3) an imidazolidinyl group of the formula

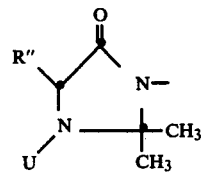

in which R" is as defined above and U is nitroso or acetyl; or R is
(4) an imido group of the formula

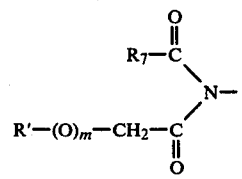

in which R' is as defined above, m is 0 or 1, and R$_7$ is C$_1$-C$_3$ alkyl, C$_1$-C$_3$ haloalkyl, C$_1$-C$_3$ alkoxy, or 2,2,2-trichloroethoxy.

2. Process of claim 1, in which R is
(1) an imido group of the formula

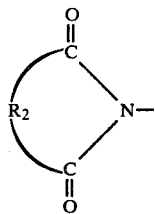

in which $R_2$ is $C_2$-$C_4$ alkenylene or 1,2-phenylene;

(2) an amido group of the formula

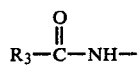

in which $R_3$ is (a) hydrogen, $C_1$-$C_3$ alkyl, halomethyl, cyanomethyl, benzyloxy, 4-nitrobenzyloxy, t-butoxyloxy, 2,2,2-trichloroethoxy, 4-methoxybenzyloxy, 3-(2-chlorophenyl)-5-methylisoxazol-4-yl;

(b) the group R' in which R' is phenyl or phenyl substituted with 1 or 2 halogens, protected hydroxy, nitro, cyano, trifluoromethyl, $C_1$-$C_4$ alkyl, or $C_1$-$C_4$ alkoxy; or (c) a group of the formula $R''$-$(Q)_m$-$CH_2$- in which R'' is R' as defined above, 1,4-cyclohexadienyl, 2-thienyl, or 3-thienyl; m is 0 or 1; and Q is O or S; subject to the limitation that when m is 1, R'' is R';

(3) an imidazolidinyl group of the formula

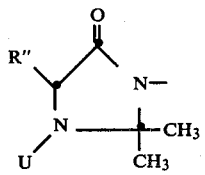

in which R'' is as defined above and U is nitroso or acetyl; or R is (4) an imido group of the formula

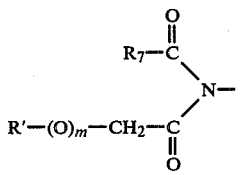

in which R' is as defined above, m is 0 or 1, and $R_7$ is $C_1$-$C_3$ alkyl, $C_1$-$C_3$ haloalkyl, $C_1$-$C_3$ alkoxy, or 2,2,2-trichloroethyl.

3. Process of claim 2, in which R is a group of the formula

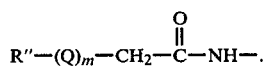

4. Process of claim 3, in which R'' is R'.
5. Process of claim 4, in which R' is phenyl.
6. Process of claim 5, in which m is 0.
7. Process of claim 5, in which m is 1.
8. Process of claim 7, is which Q is oxygen.

9. Process of claim 3, in which R'' is 2-thienyland m is zero.

10. Process of claim 1, in which $R_1$ is $C_1$-$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, dimethylallyl, phenacyl, or p-halophenacyl.

11. Process of claim 10, in which $R_1$ is methyl, benzyl, p-nitrobenzyl, p-methoxybenzyl, benzhydryl, or 2,2,2-trichloroethyl.

12. Process of claim 1, in which the reaction is carried out in the presence of a non-alkaline acid scavenger.

13. Process of claim 1, in which the non-alkaline acid scavenger is propylene oxide.

14. Process of claim 1, in which the reaction is carried out in the presence of toluene as solvent.

15. Process of claim 1, in which the N-chloro halogenating agent is a compound of the formula

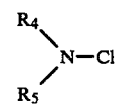

in which $R_4$ is hydrogen, chloro, $C_1$-$C_3$ alkyl, cyclohexyl, phenyl, or phenyl substituted with chloro, bromo, methyl, or nitro, and $R_5$ is $R_6$-X- in which $R_6$ is $C_1$-$C_3$ alkyl, cyclohexyl, phenyl, or phenyl substituted with chloro, bromo, methyl, or nitro, and X is

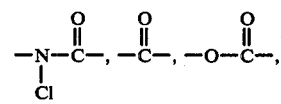

or —$SO_2$—; or $R_4$ and $R_5$ taken together with the nitrogen to which they are bonded define a heterocyclic structure of the formula

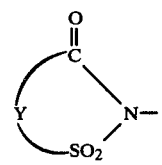

in which Y is o-phenylene, or —$(CH_2)_n$— in which n is 2 or 3; or a structure of the formula

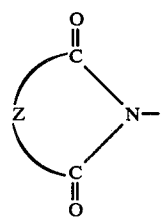

in which Z is Y as hereinbefore defined or a group of the formula

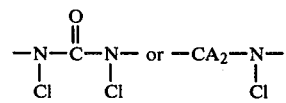

in which A is hydrogen or methyl.

16. Process of claim 15, in which the N-chloro halogenating agent has the formula

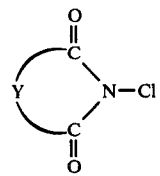

in which Y is o-phenylene or —CH$_2$—C$_2$—.

17. Process of claim 16, in which the N-chloro halogenating agent is N-chlorosuccinimide.

18. Process of claim 16, in which the N-chloro halogenating agent is N-chlorophthalimide.

19. Process of claim 15, in which the N-chloro halogenating agent is ethyl dichlorourethane.

* * * * *

UNITED STATES PATENT AND TRADEMARK OFFICE
CERTIFICATE OF CORRECTION

PATENT NO. : 4,165,315
DATED : August 21, 1979
INVENTOR(S) : Stjepan Kukolja

It is certified that error appears in the above-identified patent and that said Letters Patent are hereby corrected as shown below:

Column 5, line 16, "-(t-butoxycarbonylamino)--" should read --α-(t-butoxycarbonylamino)--.

Column 5, line 17, "-(t-butyoxycarbonylamino)" should be deleted.

Column 14, line 9, "on the solvent" should read --in the solvent--.

Column 26, line 33, "6-azetamido" should read --6-acetamido--.

Column 27, line 25, "3-methylcephem" should read --3-methylenecepham--.

Column 28, line 3, "excess of oxone" should read --excess of ozone--.

Column 30, line 14, "in which Rhd 2 is" should read --in which $R_2$ is--.

Column 31, line 20, "t-butoxyloxy," should read --t-butyloxy,--.

Signed and Sealed this

Eighth Day of April 1980

[SEAL]

Attest:

SIDNEY A. DIAMOND

Attesting Officer  Commissioner of Patents and Trademarks